United States Patent [19]
Thomissen

[11] Patent Number: 6,087,494
[45] Date of Patent: Jul. 11, 2000

[54] DEPOLYMERIZATION OF POLYAMIDES

[75] Inventor: Petrus J. H. Thomissen, Lanaken, Netherlands

[73] Assignee: DSM N.V., Heerlen, Netherlands

[21] Appl. No.: 09/069,204

[22] Filed: Apr. 29, 1998

[30] Foreign Application Priority Data

May 1, 1997 [NL] Netherlands ............... 1005942

[51] Int. Cl.[7] .............................................. C07D 201/12
[52] U.S. Cl. ........................................................... 540/540
[58] Field of Search ............................................. 540/540

[56] References Cited

U.S. PATENT DOCUMENTS

| | | | |
|---|---|---|---|
| 3,182,055 | 5/1965 | Bonfield et al. | 260/239.3 |
| 3,925,365 | 12/1975 | Izawa et al. | 260/239.3 |
| 4,311,642 | 1/1982 | Crescentini et al. | 260/239.3 |
| 4,582,642 | 4/1986 | Crescentini et al. | 540/540 |
| 5,233,037 | 8/1993 | Nielinger et al. | 540/540 |
| 5,266,694 | 11/1993 | Moran, Jr. | 540/540 |
| 5,359,062 | 10/1994 | Fuches et al. | 540/540 |
| 5,455,346 | 10/1995 | Kopietz et al. | 540/540 |
| 5,457,197 | 10/1995 | Sifniades et al. | 540/540 |
| 5,495,015 | 2/1996 | Bassler | 540/540 |
| 5,536,831 | 7/1996 | Kopietz | 540/540 |
| 5,656,757 | 8/1997 | Jenczewski et al. | 540/540 |
| 5,668,277 | 9/1997 | Hendrix et al. | 540/540 |

FOREIGN PATENT DOCUMENTS

| | | |
|---|---|---|
| 127766 | 6/1968 | Czechoslovakia . |
| 676394 | 10/1995 | European Pat. Off. . |
| 737666 | 10/1996 | European Pat. Off. . |
| 50-123689 | 9/1975 | Japan . |
| 151378 | 8/1990 | Netherlands . |
| WO 9706137 | 2/1997 | Netherlands . |
| 58795 | 12/1975 | Romania . |

*Primary Examiner*—Mukund J. Shah
*Assistant Examiner*—Bruck Kifle
*Attorney, Agent, or Firm*—Pillsbury Madison & Sutro Intellectual Property Group

[57] ABSTRACT

Process for the depolymerization of one or more polyamides into its monomeric components in the presence of water by means of at least one alkali metal compound, at least one alkaline-earth metal compound or a combination thereof. The depolymerization takes place at a pressure of between 0.2 and 2.0 MPa, so that high conversions are achieved and the depolymerization reaction proceeds faster, even in the presence of a high content of cyclic oligomers.

19 Claims, No Drawings

DEPOLYMERIZATION OF POLYAMIDES

BACKGROUND OF THE INVENTION

1. Field of the Invention

The invention relates to a process for the depolymerization of one or more polyamides into monomeric components in the presence of water by means of at least one alkali metal compound, at least one alkaline-earth metal compound or a mixture thereof.

2. Description of Related Art

Such a process is known from U.S. Pat. No. 5,359,062, which describes a process in which nylon-6 is depolymerized by means of sodium hydroxide. However, this depolymerization takes place at a pressure of more than 2 MPa. The conversions achieved are relatively low. In the example, conversion of nylon 6 to caprolactam of only 65% is achieved during 5 hours at a pressure of 5 MPa.

The reprocessing of polyamides (production waste for instance) has taken place for about 40 years, and is carried out in particular at polyamide producers and polyamide fiber spinners. In practice, this product reprocessing still takes place by means of the so-called phosphoric acid route. This means that the polyamide is depolymerized by means of steam with phosphoric acid as the catalyst, as described in, for instance, U.S. Pat. No. 3,182,055. The drawback of this route is, however, that phosphate-containing production waste is formed, which in turn must either be worked up or be disposed of as waste.

Depolymerization of polyamides is relevant for the reprocessing, for example, fibers, films, chips and, injection molded or extruded polyamide products. Of course, the commercial feasibility of reprocessing polyamide-containing waste is directly dependent on the economic/technical possibility of converting the polyamide component of this waste into monomeric components which can, preferably, without further conversion reactions, be reused. For nylon-6 the monomeric components are caprolactam and caprolactam precursors. Precursors are understood to be those compounds which can be used for the preparation of the polyamides without first having to be converted into caprolactam. An example of a precursor is amino caproic acid. In the case of nylon-6,6 the monomeric components are hexamethylene diamine and adipic acid.

Examples of polyamides which can be depolynurized according to the invention are nylon-6, nylon-6,6, nylon-4,6, nylon-12, nylon-4,12, nylon-6,12, nylon-8, etc. In this patent application, polyamides are understood to be both polymers and oligomers of amides. Oligomers are understood to be both linear and cyclic oligomers of, for instance but not limited to, caprolactam. They are also understood to be polyamide-containing mixtures. The mixtures may also include compounds such as, for instance, colorants, UV stabilizers, matting agents, antistatic agents, impact modifiers, heat stabilizers, dirt-repelling additives, spinfinish oil, and other additives.

There is, therefore, a need for a process for the depolymerization of one or more polyamides into its monomeric components with a higher and faster rate of conversion without the environmental hazards of the prior processes.

SUMMARY OF THE INVENTION

It is, therefore, an object of the invention to provide a process which yields a higher and faster conversion of one or more polyamides into its monomeric components.

It is also an object of the invention to provide a process which yields conversion of one or more polyamides into monomeric components thereof, without producing environmentally hazardous byproducts.

This object is achieved by the depolymerization of one or more polyamides in the presence of water by means of at least one alkali metal compound, at least one alkaline-earth metal compound or a combination of an alkali metal compound and an alkaline earth metal compound at a pressure of between about 0.2 and about 2.0 MPa.

Depolymerization preferably takes place at a pressure of between 0.5 and 1.8 MPa.

This results in higher conversions being achieved while, in addition, the depolymerization reaction proceeds faster, even when the polyamide has a high content of cyclic oligomers which are much more troublesome to depolymerize than the polyamide. By carrying out the depolymerization according to the present invention, the depolymerization process becomes much more efficient and cost effective because a larger amount of polyamide can be processed per unit of time.

The foregoing and other objects, features, and advantages of the present invention will become apparent from the following detailed description and claims.

DETAILED DESCRIPTION OF THE INVENTION

In the following, the process of the invention will be discussed in more detail.

The process of the invention relates to depolymerization of one or more polyamides into its monomeric components in the presence of water by means of at least one alkali metal compound, at least one alkaline-earth metal compound or a combination of an alkali metal compound and an alkaline earth metal compound. The depolymerization is conducted at a pressure of between about 0.2 to about 2.0 MPa.

Suitable alkali metal compounds or alkaline-earth metal compounds are alkali metal oxides or alkaline-earth metal oxides, alkali metal hydroxides or alkaline-earth metal hydroxides, alkali metal carbonates or alkaline-earth metal carbonates and the alkali metal salts or alkaline-earth metal salts of amino caproic acid or the metal salts of linear dimer or trimer of amino caproic acid, rare-earth alkali metal hydroxides, rare-earth alkali metal carbonates or mixtures of these compounds. Examples of such compounds are sodium oxide, potassium oxide, magnesium oxide, calcium oxide, sodium hydroxide, potassium hydroxide, calcium hydroxide, sodium carbonate, potassium carbonate, magnesium carbonate, sodium amino caproate, the sodium salt of the linear dimer or trimer of amino caproic acid, potassium amino caproate, the potassium salt of the linear dimer or trimer of amino caproic acid or a mixture thereof. Preferably, sodium hydroxide and/or sodium amino caproate is used.

The amount of alkali metal compound(s) and/or alkaline-earth metal compound(s) is generally at least 0.1 wt. % relative to the amount of polyamide to be depolymerized. Preferably, at least 0.2 wt. % of alkali (alkaline-earth) metal compound is used. In general, the amount of alkali and/or alkaline-earth metal compound(s) used does not exceed 2 wt. % of the alkali and/or alkaline-earth metal compound(s) used.

The depolymerization is carried out by passing steam through the polyamide. The steam has a temperature of between about 220° C. and about 450° C. Preferably, the temperature of the steam is between about 250° C. and about 350° C. The amount by weight of steam per hour is less than or equal to 3.5 times the amount by weight of polyamide.

Preferably, the amount of steam per hour is less than or equal to 2.5 times the amount by weight of polyamide. More preferably, the amount by weight of steam is the same as the amount by weight of polyamide.

The reaction temperature, i.e. the temperature of the molten polyamide, at which the process for the depolymerization according to the present invention is carried out, is between about 200° C. and about 400° C. Preferably, the temperature is between about 250° C. and about 350° C., and more preferably the temperature is between about 250° C. and about 300° C.

Before the polyamide is contacted with the superheated steam, the polyamide is preferably molten. Melting preferably takes place in the absence of air (oxygen). The molten polyamide is depolymerized into its monomeric components. These monomeric components are discharged via a gas phase. In practice, the gas phase is then condensed to a condensate. It is possible to purify the condensate by hydrogenation or by a potassium permanganate treatment. The drawback of purification by means of a potassium permanganate treatment is that pyrolusite is formed. Preferably, therefore, use is made of hydrogenation, as described in U.S. Pat. No. 5,556,890 (EP-A-627417), the entire disclosures of which is herein incorporated by reference. A major advantage of depolymerization with the aid of alkali metal compound(s) and/or alkaline-earth metal compound(s) in combination with the purification by means of hydrogenation is that little or no waste is formed which requires subsequent processing. Therefore, the present process in both economical and practical.

This condensate may also contain linear and cyclic oligomers. These oligomers can be separated from the monomeric components, for instance by means of distillation as customarily employed by methods well known to those of ordinary skill in the art. The residue, including among other things, the alkali metal compound(s) and/or alkaline-earth metal compound(s), that remains after the distillation of the monomeric components, can be recycled to the depolymerization reactor.

The process according to the present invention is eminently suitable for the processing of polyamide-containing waste; preferably, the waste is, if necessary, first mechanically reduced in size by, for instance, milling, chopping, tearing and/or cutting.

Depolymerization according to the invention can be effected batchwise, semi-continuously or continuously.

The invention will be elucidated on the basis of the following non-restrictive examples.

EXAMPLES

Comparative Experiment A

One liter of water and 100 g of nylon-6 were introduced into an autoclave. 0.5 g of sodium hydroxide was added. By means of nitrogen, the pressure in the autoclave was raised to 0.5 MPa. Then the temperature was raised to 250° C. with stirring. The autoclave was operated at a pressure of 5 MPa during the depolymerization. After 5 hours, the autoclave was cooled down to room temperature. After extraction with toluene the solvent was removed by means of distillation of the organic phase. The residue contained only 65 g of caprolactam. 30 g of the non-converted polyamide remained behind in the extracted aqueous phase.

Example I and Comparative Experiments B and C

An amount of polyamide feed and a catalyst were introduced into an autoclave. The autoclave was then heated to a temperature of 270° C. The autoclave had a feed line through which 3.5 kg of steam per hour was dosed per kg of polyamide feed. The steam leaving the autoclave was cooled down so that condensation occurred. The monomeric components of the polyamide were recovered by means of vacuum distillation. The content of monomeric components was then determined by means of a refractive index measurement. To this end a 100 ml sample was drawn from the distillate and heated at a temperature of 20° C. in a thermostatted bath for 1 hour. The sample was then placed on the prism of a refractometer supplied by Tamson B. V. (Netherlands) and the refractive index was read after 1 minute. This was repeated. The two measurements were not allowed to deviate by more than 0.0002. The refractive index

TABLE I

|  | Example I | Comparative Experiment B | Comparative Experiment C |
| --- | --- | --- | --- |
| feed | 160 g nylon-6 chips + 40 g cyclic oligomers | 200 g nylon-6 chips | 200 g cyclic oligomers |
| catalyst | 0.15 wt. % NaOH | 3 wt. % $H_3PO_4$ | 3 wt. % $H_3PO_4$ |
| p (MPa) | 1.8 | 0.1 | 0.1 |
| reaction time (min) | 195 | 223 | 248 |
| conversion to caprolactam (%) | 98.6 | 96.1 | 65.3 |

From Table I it is evident that the conversion is significantly lower when the starting material was cyclic oligomers as compared to nylon-6 chips. Although a good conversion to caprolactam is achieved with $H_3PO_4$, the drawback was that 14 g of phosphate waste remained behind after the depolymerization. In contrast, Example I, according to the invention, produces no phosphate waste and produces a higher rate of conversion to caprolactam.

Comparison of Example I and Comparative Experiment A teaches that the conversion is many times higher at substantially lower pressures, and is moreover achieved much faster. In addition, no toluene or other organic solvent is needed to recover the caprolactam. This results in an environmentally safer and less costly process.

What is claimed is:

1. A process for depolymerization of one or more polyamides into monomeric units, comprising:

depolymerizing said one or more polyamides at a pressure of between about 0.2 and about 2.0 MPa in the presence of at least one alkali metal compound, at least one alkaline-earth metal compound or a mixture thereof;

wherein said depolymerization is carried out by passing steam through said one or more polyamides and discharging said monomeric units in a gas phase.

2. The process of claim 1, wherein the depolymerization pressure is between 0.5 and 1.8 MPa.

3. The process of claim 1, wherein the metal compound is at least one compound selected from the group consisting of alkali metal oxides, alkaline-earth metal oxides, alkali metal hydroxides, alkaline-earth metal hydroxides, alkali metal carbonates, alkaline-earth metal carbonates, alkali metal salts of linear dimer or trimer of amino caproic acid and alkaline-earth metal salts of linear dimer or trimer of amino caproic acid, alkali metal salts of amino caproic acid and alkaline-earth metal salts of amino caproic acid.

4. The process of claim 3, wherein the metal compound is at least one member selected from the group consisting of sodium oxide, potassium oxide, magnesium oxide, calcium oxide, sodium hydroxide, potassium hydroxide, calcium hydroxide, sodium carbonate, potassium carbonate, magnesium carbonate, sodium amino caproate, a sodium salt of linear dimer or trimer of amino caproic acid, potassium amino caproate, potassium salt of linear dimer or trimer of amino caproic acid, and a mixture thereof.

5. The process of claim 4, wherein the metal compound is sodium hydroxide and sodium amino caproate.

6. The process of claim 4, wherein the metal compound is sodium hydroxide or sodium amino caproate.

7. The process of claim 1, wherein the metal compound is present in an amount of 0.1 wt. % to 2 wt. % relative to the amount of polyamide to be depolymerized.

8. The process of claim 7, wherein the metal compound is present in an amount of about 0.2 wt. % relative to the amount of polyamide to be depolymerized.

9. The process of claim 1, wherein the depolymerization is carried out by passing steam at a temperature of between about 220° C. and about 450° C. through the polyamide.

10. The process of claim 9, wherein the steam has a temperature of between about 250° C. and about 350° C.

11. The process of claim 9, wherein the amount of steam per hour is less than or equal to 3.5 times the amount of polyamide.

12. The process of claim 10, wherein the amount of steam per hour is less than or equal to 3.5 times the amount of polyamide.

13. The process of claim 11, wherein the amount of steam per hour is less than or equal to 2.5 times the amount of polyamide.

14. The process of claim 12, wherein the amount of steam per hour is less than or equal to 2.5 times the amount of polyamide.

15. The process of claim 1, wherein the depolymerization takes place at a reaction temperature of between about 200° C. and about 400° C.

16. The process of claim 1, further comprising purifying the monomeric components by means of hydrogenation after the step of depolymerizing.

17. The process of claim 1, further comprising recycling any metal compound remaining after the depolymerization process.

18. The process of claim 1, wherein the polyamide contains cyclic oligomers.

19. A process for the depolymerization of one or more polyamides into monomeric components, comprising:

depolymerizing the one or more polyamides at a temperature of 270° C. and at a pressure of 1.8 MPa by passing steam through said one or more polyamides in an amount of steam per hour equaling 3.5 times an amount of polyamide feed, in the presence of sodium hydroxide wherein the monomeric units are discharged in the gas phase.

* * * * *